US010136811B2

(12) United States Patent
Sudo

(10) Patent No.: US 10,136,811 B2
(45) Date of Patent: Nov. 27, 2018

(54) FUNDUS IMAGING APPARATUS AND METHOD FOR CONTROLLING THE SAME, AND STORAGE MEDIUM

(71) Applicant: CANON KABUSHIKI KAISHA, Tokyo (JP)

(72) Inventor: Takashi Sudo, Inagi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 118 days.

(21) Appl. No.: 15/432,812

(22) Filed: Feb. 14, 2017

(65) Prior Publication Data

US 2017/0231492 A1 Aug. 17, 2017

(30) Foreign Application Priority Data

Feb. 17, 2016 (JP) ................. 2016-028252

(51) Int. Cl.
*A61B 3/12* (2006.01)
*A61B 3/00* (2006.01)
*A61B 3/10* (2006.01)
*A61B 3/14* (2006.01)
*G02B 27/00* (2006.01)

(52) U.S. Cl.
CPC ............. *A61B 3/12* (2013.01); *A61B 3/005* (2013.01); *A61B 3/0025* (2013.01); *A61B 3/0091* (2013.01); *A61B 3/1005* (2013.01); *A61B 3/1015* (2013.01); *A61B 3/14* (2013.01); *G02B 27/0068* (2013.01)

(58) Field of Classification Search
CPC ....... A61B 3/12; A61B 3/1015; A61B 3/0091; A61B 3/005; A61B 3/0025; A61B 3/14; A61B 3/1005; G02B 27/0068
See application file for complete search history.

(56) References Cited

FOREIGN PATENT DOCUMENTS

JP 2012-176093 A 9/2012
JP 2015-104468 A 6/2015

*Primary Examiner* — Jack Dinh
(74) *Attorney, Agent, or Firm* — Canon U.S.A., Inc. IP Division

(57) ABSTRACT

A fundus imaging apparatus according to embodiments of the present invention includes an optical unit configured to guide light from a fiber light source to a fundus of a subject eye, a wavefront sensor capable of measuring the wavefront of reflected light guided via the optical unit after the light from the fiber light source is reflected on the fundus, a wavefront correction device provided on an optical path extending between the fiber light source and the subject eye to correct the wavefront of the reflected light, an APD that can receive the reflected light and capture an image of the fundus, and a processing and control unit configured to acquire thickness information about an optical diffusive layer of the fundus and determine a correction value to be used when the wavefront correction device corrects the wavefront of the reflected light based on the acquired thickness information.

10 Claims, 12 Drawing Sheets

FUNDUS IMAGING APPARATUS AND METHOD FOR CONTROLLING THE SAME, AND STORAGE MEDIUM

BACKGROUND

Field of the Invention

The present disclosure relates to a fundus imaging apparatus that can capture a fundus image of a subject eye, a method for controlling the fundus imaging apparatus, and a storage medium storing a program for causing a computer to realize the control method.

Description of the Related Art

An aberration correction technique for correcting aberration of a subject eye is conventionally known and applied to a fundus imaging apparatus, according to which a wavefront sensor disposed at a position conjugate with a pupil of the subject eye detects the wavefront of reflected light when the light is projected and reflected on a fundus of the subject eye and a correction device is controlled in such a way as to correct aberration of the detected wavefront of the reflected light. The above-mentioned aberration correction technique is applicable to the imaging of a micro portion on the fundus of the subject eye with high resolution. For example, the captured micro portion image can be used to diagnose information about the shape and density of a photoreceptor cell and the flow of blood corpuscles for the purpose of research.

For example, an ophthalmology apparatus discussed in Japanese Patent Application Laid-Open No. 2015-104468 includes a scanning unit configured to perform scanning by projecting measurement light on the fundus of a subject eye, an adjustment unit configured to perform focus adjustment for the measurement light projected on the fundus at a plurality of imaging planes in an optical axis direction, a correction unit configured to correct the aberration occurring in the subject eye, and an image capturing unit configured to capture images of the plurality of imaging planes. The ophthalmology apparatus calculates a focus shift amount between a focus position for acquiring an image of a first imaging plane and a focus position for acquiring an image of a second imaging plane, spaced from the first imaging plane by a predetermined distance in the optical axis direction, according to diopter of the subject eye. The adjustment unit performs the focus adjustment according to the calculation result. The above-mentioned configuration discussed in Japanese Patent Application Laid-Open No. 2015-104468 is useful to capture an image of the fundus of the subject eye with high image quality.

Further, a technique capable of measuring the blood flow of a blood vessel is, for example, discussed in Japanese Patent Application Laid-Open No. 2012-176093. The discussed technique includes identifying a blood vessel region of an imaging target, identifying information relating to the blood flow velocity of the blood vessel based on a Scanning LASER Ophthalmoscope (SLO) image generated by a signal light obtained at a focus position deeper than the blood vessel region, and acquiring information relating to the blood flow of the blood vessel based on the identified region and the information relating to the blood flow velocity.

However, when a fundus of a subject eye is imaged according to the above-mentioned conventional technique, if the thickness of an optical diffusive layer of the fundus is greater at a peripheral portion compared to a central portion, a problem that the image quality of the peripheral portion deteriorates greatly compared to the central portion may occur. In this respect, the inventor believes that a physical structure of the optical diffusive layer of the fundus of the subject eye and a related optical function possibly induce the problem that the image quality deteriorates greatly at the peripheral portion of the fundus.

SUMMARY OF THE INVENTION

The present invention is directed to a technique capable of improving the image quality of an image obtainable by capturing a fundus of a subject eye.

Embodiments of the present invention include a fundus imaging apparatus can capture a fundus image of a subject eye. The fundus imaging apparatus includes an optical unit configured to guide light from a light source to a fundus, a wavefront measurement unit configured to measure the wavefront of reflected light guided via the optical unit after the light is reflected on the fundus, a wavefront correction unit provided on an optical path extending between the light source and the subject eye and configured to correct the wavefront, an image-capturing unit configured to receive the reflected light and capture an image of the fundus, an acquisition unit configured to acquire thickness information about an optical diffusive layer of the fundus, and a determination unit configured to determine a correction value to be used when the wavefront correction unit corrects the wavefront based on the thickness information.

Further, embodiments of the present invention provide a method for controlling the above-mentioned fundus imaging apparatus, and a storage medium storing a program that causes a computer to execute the control method.

Further features of the present invention will become apparent from the following description of exemplary embodiments with reference to the attached drawings.

DESCRIPTION OF THE EMBODIMENTS

Hereinbelow, exemplary embodiments of the present invention will be described in detail with reference to attached drawings.

Prior to the description of each exemplary embodiment of the present invention, described in detail below is a phenomenon that the image quality deteriorates at a peripheral portion of a fundus in a fundus image captured the subject eye.

Figure 1A:
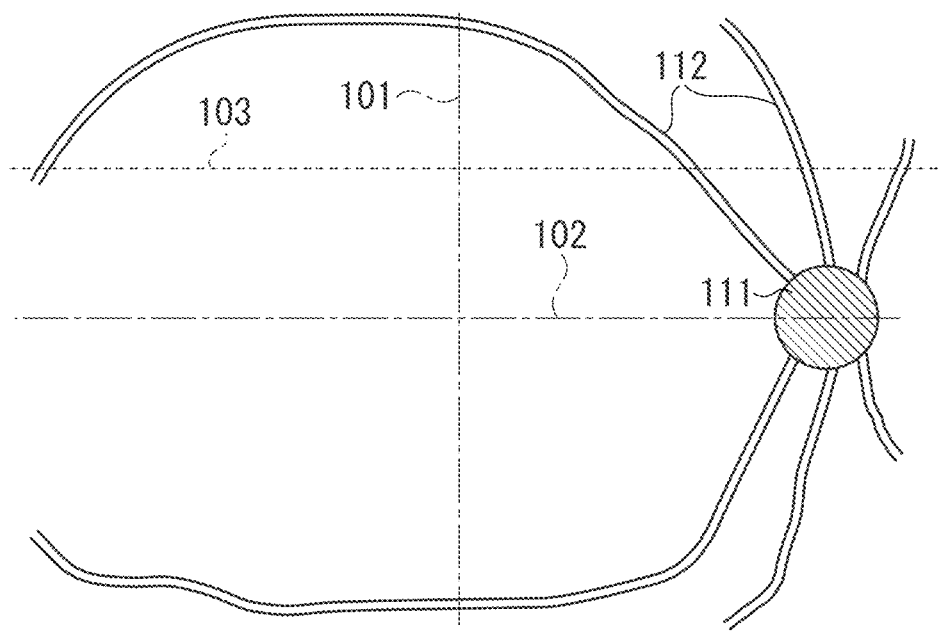
FIGS. 1A and 1B schematically illustrate a fundus configuration of a subject eye (e.g., a right eye).
Figure 1B:
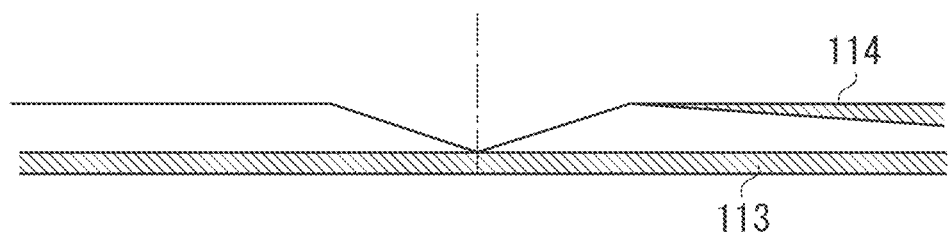

FIGS. 1A and 1B schematically illustrate a fundus configuration of a subject eye (e.g., a right eye).

A wide-angle imaging optical system that captures an image of a wide-angle region of the fundus illustrated in FIGS. 1A and 1B is an optical system that is different from the optical system of a fundus imaging apparatus according to an exemplary embodiment of the present invention. A resolution to be set in capturing the above-mentioned wide-angle region is lower than a resolution to be set in performing wavefront (i.e., wavefront aberration) correction. The resolution setting value is determined with reference to conditions such as entrance pupil diameter and no aberration correction.

In FIG. 1A, a dashed-dotted line 101 indicates a vertical center line of the fundus that extends in the up-and-down direction and a dashed-dotted line 102 indicates a horizontal center line of the fundus that extends in the right-and-left direction. Further, FIG. 1A includes an example illustration of an optic disk 111 and a blood vessel 112, which is referred to as "arcade blood vessel". In FIG. 1A, a horizontal direction is a right-and-left direction of the subject eye and a vertical direction is a direction perpendicular to the horizontal direction.

FIG. 1B illustrates a cross-sectional view of a retina in a thickness direction (i.e., in the depth direction), which is taken along a dotted line 103 illustrated in FIG. 1A. FIG. 1B includes an example illustration of a photoreceptor cell layer (IS/OS) 113 and a nerve fiber layer (NFL) 114. As illustrated in FIG. 1B, the thickness of the photoreceptor cell layer 113 is symmetrical in the right and left direction. On the other hand, the thickness of the nerve fiber layer 114 is asymmetrical in the right and left direction. In particular, the nerve fiber layer 114 is very thin on the left side thereof. The thickness of the nerve fiber layer 114 gradually increases when the position approaches a right peripheral region of the retina where the optic disk 111 is present. It is known beforehand that the thickness of the nerve fiber layer 114 increases up to 200 μm to 300 μm at the right side thereof. According to a detailed investigation on captured photoreceptor cell images, it has been confirmed that the image quality of the nerve fiber layer 114 deteriorates at the thicker portion thereof. In other words, as an investigation result relating to a correlation between the position of a fundus and the image quality of a captured image, it has been confirmed that the image quality of a captured image depends on the thickness of the nerve fiber layer 114. The principle of the above-mentioned phenomenon will be described in detail below.

First, a first exemplary embodiment of the present invention will be described in detail below.

Figure 2:
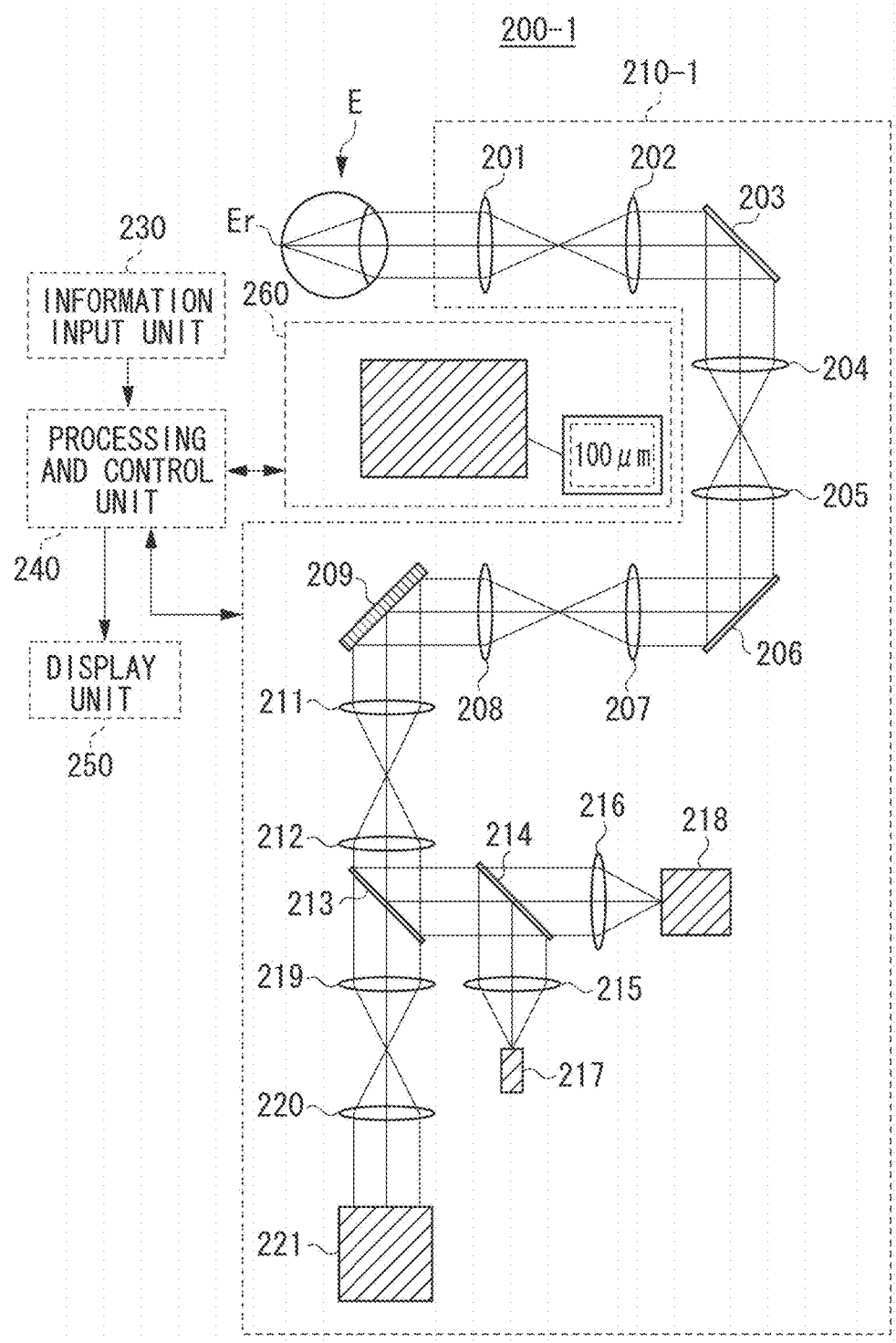
FIG. 2 illustrates an example of a schematic configuration of a fundus imaging apparatus according to a first exemplary embodiment of the present invention.

FIG. 2 illustrates an example of a schematic configuration of a fundus imaging apparatus 200-1 according to the first exemplary embodiment of the present invention. The fundus imaging apparatus 200-1 can capture an image of fundus Er of subject eye E.

As illustrated in FIG. 2, the fundus imaging apparatus 200-1 includes a fundus imaging unit 210-1, an information input unit 230, a processing and control unit 240, a display unit 250, and a thickness information acquisition unit 260.

The fundus imaging unit 210-1 includes lenses 201, 202, 204, 205, 207, 208, 211, 212, 215, 216, 219, and 220. Further, the fundus imaging unit 210-1 includes a scanner 203 that performs scanning in a main scanning direction and a scanner 206 that performs scanning in a sub scanning direction. In addition, the fundus imaging unit 210-1 includes a wavefront correction device 209, beam splitters 213 and 214, a fiber light source 217, an avalanche photodiode (APD) 218, and a wavefront sensor 221.

The above-mentioned lenses establish a conjugate relationship between the retina of the subject eye E and the fiber light source 217 and a conjugate relationship between the retina of the subject eye E and the APD 218. Further, the above-mentioned lenses establish a conjugate relationship between the pupil of the subject eye E and the wavefront sensor 221 and a conjugate relationship between the pupil of the subject eye E and the wavefront correction device 209, as well as a conjugate relationship between the pupil of the subject eye E and the scanners 203 and 206. The beam splitters 213 and 214 can split the optical path for each of the wavefront sensor 221, the fiber light source 217, and the APD 218. The above-mentioned lenses and beam splitters cooperatively constitute an optical unit configured to guide the light from the fiber light source 217 to the fundus Er.

The scanners 203 and 206 are provided between the fiber light source 217 and the subject eye E. Each of the scanners 203 and 206 is a scanning unit configured to scan the light emitted from the fiber light source 217 toward the region of the fundus Er.

The wavefront sensor 221 is a wavefront measurement unit configured to measure the wavefront (i.e., wavefront aberration) of reflected light when the reflected light is guided via the above-mentioned optical unit after the light is emitted from the fiber light source 217 and reflected on the fundus Er.

The wavefront correction device 209 is provided between the fiber light source 217 and the subject eye E on the optical path of the light. The wavefront correction device 209 is a wavefront correction unit configured to correct the wavefront (i.e., wavefront aberration) of the reflected light guided via the above-mentioned optical unit.

The APD 218 is an image-capturing unit configured to receive the reflected light guided via the above-mentioned optical unit and capture an image relating to the fundus Er (i.e., fundus image).

The information input unit 230 can receive information entered by a user or transmitted from an external apparatus and can send the input information to the processing and control unit 240.

For example, the processing and control unit 240 controls components constituting the fundus imaging apparatus 200-1 based on input information received from the information input unit 230. The processing and control unit 240 controls various operations to be performed by the fundus imaging apparatus 200-1. Further, the processing and control unit 240 performs various kinds of processing if necessary.

The processing and control unit 240 can control the display unit 250 to display various kinds of images and information.

The processing and control unit 240 can control the thickness information acquisition unit 260 to acquire thickness information about an optical diffusive layer of the fundus Er. More specifically, in the present exemplary embodiment, the thickness information acquisition unit 260 acquires thickness information about the nerve fiber layer 114 (i.e., the optical diffusive layer of the fundus Er positioned closest to the incoming light) when the light emitted from the fiber light source 217 enters the fundus Er, as illustrated in FIG. 1B. For example, the thickness information acquisition unit 260 is an Optical Coherence Tomography (OCT) apparatus. Although the thickness information acquisition unit 260 is not integrated with the fundus imaging unit 210-1 as illustrated in FIG. 2, the present exemplary embodiment is not limited to the illustrated example. For example, the thickness information acquisition unit 260 can be incorporated in the fundus imaging unit 210-1.

Further, if the thickness information acquisition unit 260 acquires the thickness information about the optical diffusive layer of the fundus Er (more specifically, the nerve fiber layer 114 in the present exemplary embodiment), the processing and control unit 240 determines a correction value to be used when the wavefront correction device 209 corrects the wavefront (i.e., wavefront aberration) of the reflected light based on the acquired thickness information. In this respect, the processing and control unit 240 serves as a determination unit configured to perform the above-mentioned determination processing. Then, the wavefront correction device 209 corrects the wavefront (i.e., wavefront aberration) of the reflected light based on the correction value determined by the processing and control unit 240. In this case, for example, the wavefront correction device 209 corrects the wavefront (i.e., wavefront aberration) of the reflected light that enters the APD 218.

Hereinbelow, an example procedure of image capturing processing that is performed by the fundus imaging apparatus 200-1 will be described in detail below. First, the processing and control unit 240 controls the thickness information acquisition unit 260 to measure the thickness of the nerve fiber layer 114 of the fundus Er and acquire thickness information about the nerve fiber layer 114. Next, the processing and control unit 240 determines a correction value (i.e., target value) to be used when the wavefront correction device 209 corrects the wavefront of the reflected light, based on the thickness information about the nerve fiber layer 114 acquired by the thickness information acquisition unit 260.

Next, in a state where the subject eye E is fixedly placed on the fundus imaging apparatus 200-1, the wavefront sensor 221 measures the wavefront of reflected light guided via the above-mentioned optical unit when the light is emitted from the fiber light source 217 and reflected on the fundus Er. In this case, the processing and control unit 240 performs a control to drive the scanners 203 and 206, and the wavefront sensor 221 measures the wavefront of reflected light within a predetermined angle of view.

Subsequently, the processing and control unit 240 drives the wavefront correction device 209 based on the determined correction value and corrects the wavefront of reflected light measured by the wavefront sensor 221. Then, the processing and control unit 240 controls the APD 218 to perform an image capturing operation after the wavefront correction has been performed based on the correction value determined by the wavefront correction device 209.

Figure 3:
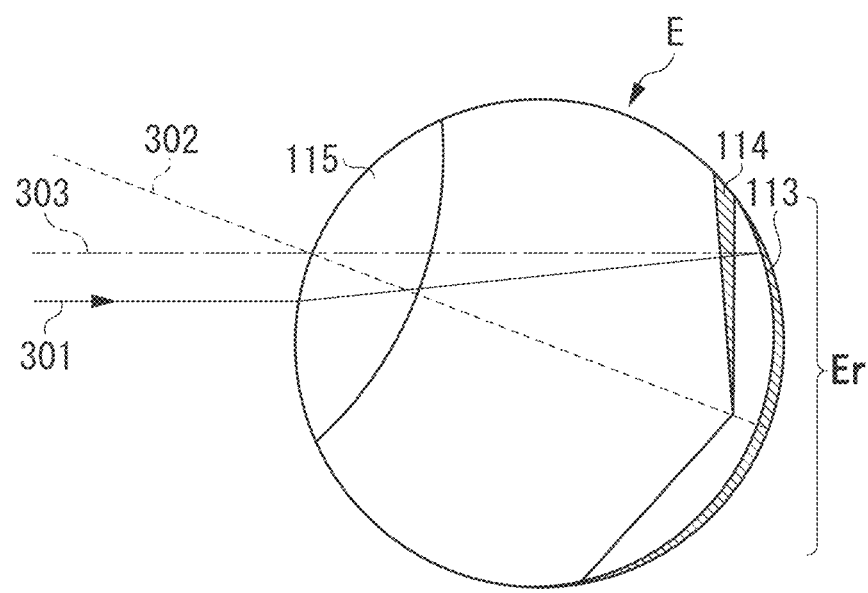
FIG. 3 illustrates an example of an optical path along which light entering the subject eye reaches a retina (i.e., the fundus) according to the first exemplary embodiment of the present invention.

FIG. 3 illustrates an example of the optical path along which the light entering the subject eye E reaches the retina (i.e., the fundus Er) according to the first exemplary embodiment of the present invention.

FIG. 3 includes a pupil 115, the fundus Er, the photoreceptor cell layer 113, and the nerve fiber layer 114 of the subject eye E. Further, FIG. 3 includes a light beam 301 emitted from the fiber light source 217, a gaze direction 302 of the subject eye E, and an optical axis 303 of the above-mentioned optical unit.

In the present exemplary embodiment, the fundus imaging apparatus causes the light beam 301 emitted from the fiber light source 217 to enter a lower part of the pupil 115 offset lower from the center thereof, for the purpose of reducing a reflection ghost generated by a cornea of the subject eye E. Due to a refraction function of the subject eye E, the light beam 301 is refracted to a direction inclined from the optical axis 303 of the optical unit. Then, the light beam 301 reaches the retina (i.e., the fundus Er).

Hereinbelow, the above-mentioned reflection ghost generated by the cornea of the subject eye E will be described in detail.

When the fundus imaging apparatus measures a central portion of the subject eye E, if the light beam 301 enters coaxially the optical axis 303 of the optical unit, and if the subject eye E is placed perpendicularly to the optical axis 303 of the optical unit, the light beam 301 reflected on the cornea of the subject eye E will returns to the fiber light source 217 along the optical path of the incoming light. In this case, the light reflected on the cornea enters the wavefront sensor 221 illustrated in FIG. 2. Therefore, measurement accuracy of the wavefront sensor 221 greatly decreases in measuring the wavefront (i.e., wavefront aberration) of the reflected light. Therefore, the fundus imaging apparatus according to the present exemplary embodiment causes the light beam 301 emitted from the fiber light source 217 to enter the subject eye E from a position shifted in the up-and-down direction from the optical axis 303 of the optical unit, i.e., from a position offset from the central position of the light-receiving pupil of above-mentioned optical unit.

Figure 4:
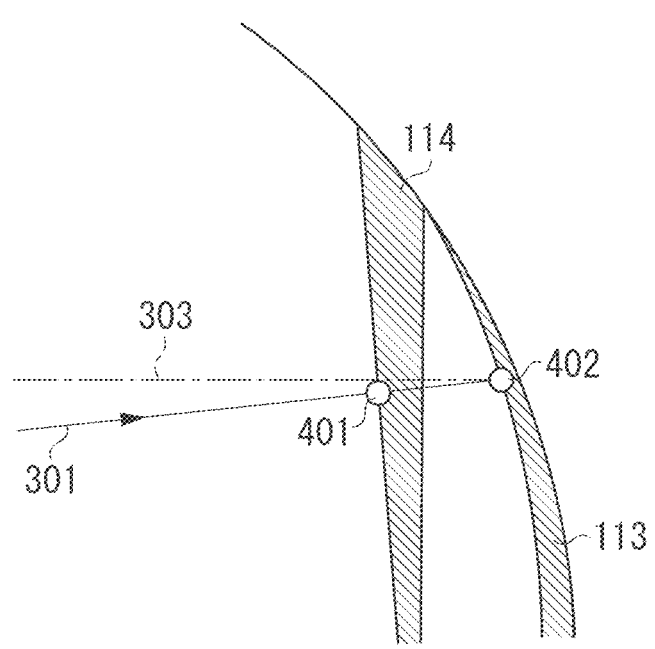
FIG. 4 is an enlarged view of the optical path illustrated in FIG. 3, along which the light reaches the fundus.

FIG. 4 is an enlarged view of the optical path illustrated in FIG. 3, along which the light beam 301 reaches the fundus Er, in a region adjacent to the retina.

As illustrated in FIG. 4, the light beam 301 enters the fundus Er along a path in an inclined manner relative to the optical axis 303 of the optical unit. The light beam 301 reaches the nerve fiber layer 114 at a point 401. The nerve fiber layer 114 is a retina surface part that causes strongest reflections. Therefore, the nerve fiber layer 114 will be described as an example.

The nerve fiber layer 114 is the optical diffusive layer of the fundus Er. Therefore, the incoming light beam 301 causes diffusion and reflection in the nerve fiber layer 114. Accordingly, the fundus imaging apparatus captures an image of the fundus Er while regarding the point 401 as a dummy light emission point. Further, after passing through the nerve fiber layer 114, the light beam 301 travels toward the fundus Er and reaches the photoreceptor cell layer 113 at a point 402 in FIG. 4. As known beforehand, the photoreceptor cell layer 113 or retinal pigment epithelium (RPE) is an optical diffusive layer that is optically equivalent to the nerve fiber layer 114. Therefore, the point 402 can be regarded as a light emission point. Accordingly, in particular, in a case where the photoreceptor cell layer 113 is focused to capture the image thereof, there are two light emission points (i.e., the dummy light emission point 401 of the nerve fiber layer 114 and the actual light emission point 402 of the photoreceptor cell layer 113) when the fundus imaging apparatus captures an image of the fundus Er. In this case, the wavefront sensor 221 measures the wavefront of the reflected light based on the light passing through at least two optical diffusive layers of the fundus Er.

Next, the principle of wavefront measurement that can be performed by the wavefront sensor 221 will be described in detail below.

Figure 5:
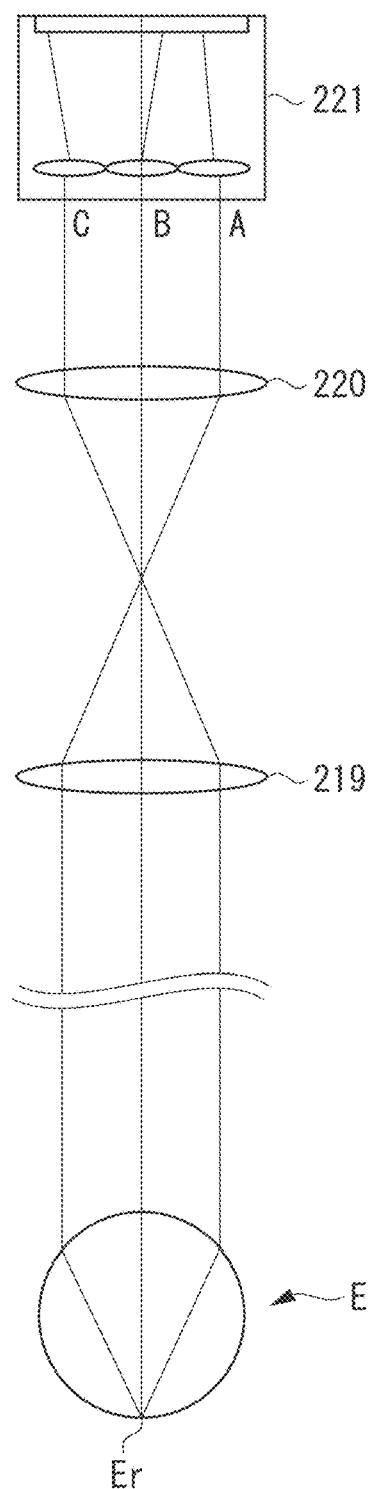
FIG. 5 illustrates a wavefront sensor that can measure the wavefront (i.e., wavefront aberration) of light reflected from the fundus of the subject eye according to the first exemplary embodiment of the present invention.

FIG. 5 illustrates the wavefront sensor 221 that measures the wavefront (i.e., wavefront aberration) of the light reflected from the fundus Er of the subject eye E according to the first exemplary embodiment of the present invention. In FIG. 5, constituent components similar to those illustrated in FIG. 2 are denoted by the same reference numerals.

In FIG. 5, positions A, B, and C in the optical path of the reflected light correspond to the angle of the light reflected on the fundus Er. In general, the light reflected on the fundus Er has an aberration, i.e., the wavefront of the reflected light is in a damaged state compared to a plane wave. The wavefront of the reflected light causes difference in incident angle at the positions A, B, and C, which can be detected as a positional deviation of the image at a light receiving portion of the wavefront sensor 221. The reason of causing light beam angular deviation at the positions A, B, and C in the case of the above-mentioned two light emission points 401 and 402 will be described in detail below.

Figure 6:
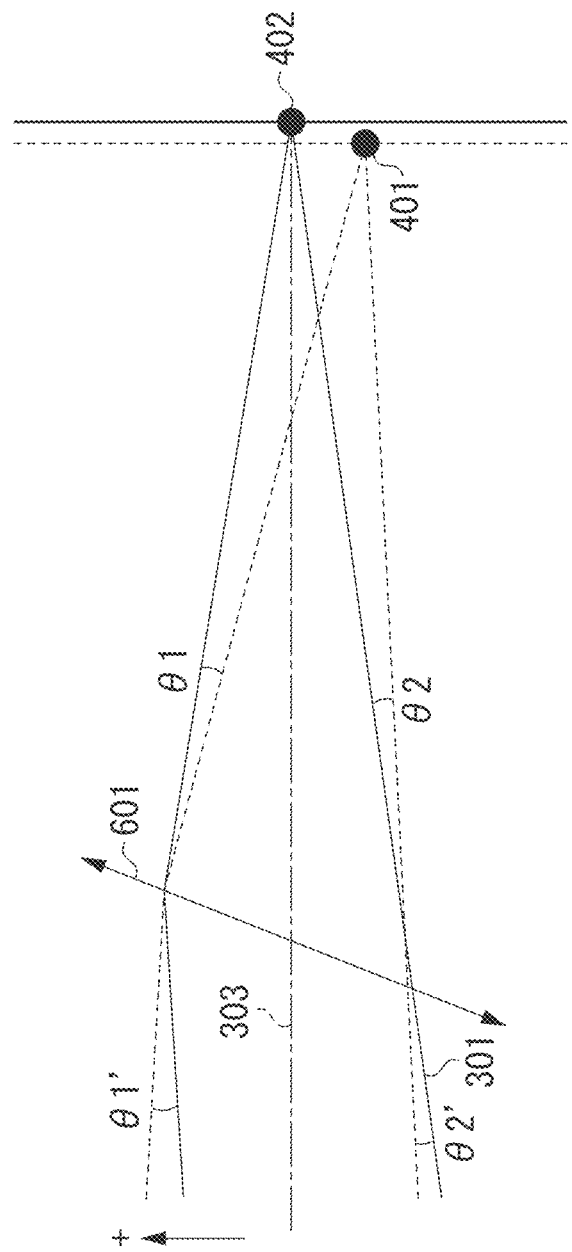
FIG. 6 illustrates the optical path of the light entering the subject eye according to the first exemplary embodiment of the present invention.

FIG. 6 illustrates the optical path of the light beam 301 entering the subject eye E according to the first exemplary embodiment of the present invention. In FIG. 6, portions similar to those illustrated in FIGS. 3 and 4 are denoted by the same reference numerals.

In FIG. 6, an eyeball refraction lens 601 expresses a refracting power of the eyeball of the subject eye E. The eyeball refraction lens 601 is inclined relative to the optical axis 303 of the optical unit in a state where the subject eye E is directed to an upper side. In this case, $\theta 1$ represents an angle formed between light beams from two light emission points 401 and 402 at the upper side of FIG. 6, and $\theta 2$ represents an angle formed between light beams from two light emission points 401 and 402 at the lower side of FIG. 6. An angular relationship $\theta 1 > \theta 2$ is established because the eyeball (i.e., the eyeball refraction lens 601) is inclined in the clockwise direction since the subject eye E is directed upward. Accordingly, an angular relationship $\theta 1' > \theta 2'$ is also established, in which $\theta 1'$ and $\theta 2'$ represent angles formed between two light beams emitted from the eyeball of the subject eye E. More specifically, measuring a portion including the photoreceptor cell layer 113 of the fundus Er is optically influenced by diffusion effects of the nerve fiber layer 114.

Figure 7:
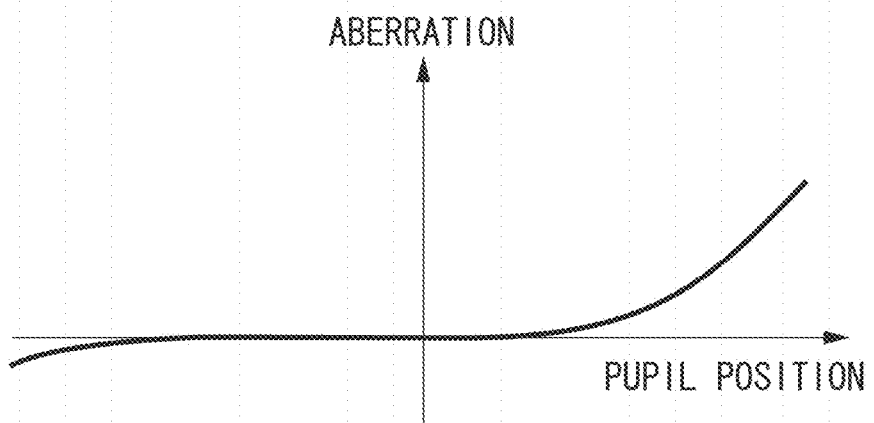
FIG. 7 illustrates lateral aberration measured by the wavefront sensor according to the first exemplary embodiment of the present invention.

FIG. 7 illustrates lateral aberration measured by the wavefront sensor 221 according to the first exemplary embodiment of the present invention. FIG. 7 indicates lateral aberration amount on a vertical axis, and pupil position on a horizontal axis.

In FIG. 7, a "plus" side of the horizontal axis is the upper side of the pupil (i.e., the "plus" side illustrated in FIG. 6). Because of the above-mentioned angular relationship $\theta 1' > \theta 2'$, the aberration becomes asymmetrical in the up-and-down direction of the pupil. Therefore, an optical compensation apparatus configured to measure an eyeball aberration with the wavefront sensor 221 and correct the eyeball aberration may erroneously measure an aberration due to adverse influence of the nerve fiber layer 114, even when the eyeball aberration is zero. Therefore, it is difficult to completely correct the eyeball aberration.

A fundus imaging apparatus according to exemplary embodiments of the present invention capable of solving the above-mentioned problem will be described in detail below. The above-mentioned problem is that the wavefront aberration is erroneously detected because of a plurality of light emission points (i.e., points 401 and 402 illustrated in FIG. 6) generated by a reflection layer represented by the nerve fiber layer 114. Therefore, if the thickness of the nerve fiber layer 114 or the influence of a damaged retina image on a wavefront aberration measurement result caused by the thickness is known beforehand, it becomes feasible to accurately correct the eyeball aberration by giving an offset amount to the correction target value of the eyeball aberration or through conversion into the aberration amount (i.e., INPUT).

In general, the aberration correction is performed in such a way as to equalize the wavefront aberration measured by the wavefront sensor 221 to zero. More specifically, Zernike coefficients are used to perform the aberration correction and each term is set to zero. However, the fundus imaging apparatus according to the present exemplary embodiment solves the above-mentioned problem by giving an offset to a numerical value of the Zernike coefficient. More specifically, the fundus imaging apparatus according to the present exemplary embodiment causes the thickness information acquisition unit 260 to acquire thickness information about the nerve fiber layer 114 and determines the correction value (i.e., target value) to be used when the wavefront correction device 209 corrects the wavefront of the reflected light based on the acquired thickness information.

By setting the lateral aberration illustrated in FIG. 7 to the correction value (i.e., target value), it is feasible to correct the aberration component that the eyeball has. In this case, it is useful to set numerical values indicated in the following table 1 (see each term marked with *) for coma aberration, spherical aberration, and tilt component.

TABLE 1

| Term | Order n | Order m | Target coefficient | |
|---|---|---|---|---|
| 1 | 0 | 0 | 0.00 | Constant term |
| 2 | 1 | 0 | 0.00 | Tilt X component |
| 3* |  | 1 | 0.20 | Tilt Y component |
| 4 | 2 | 0 | 0.00 | Astigmatism (0°, 90°) |
| 5 |  | 1 | 0.00 | Focus shift |
| 6 |  | 2 | 0.00 | Astigmatism (±45°) |
| 7 | 3 | 0 | 0.00 | |
| 8 |  | 1 | 0.00 | 3rd-order coma X component |
| 9* |  | 2 | 0.02 | 3rd-order coma Y component |
| 10 |  | 3 | 0.00 | |
| 11 | 4 | 0 | 0.00 | |
| 12 |  | 1 | 0.00 | |
| 13* |  | 2 | 0.03 | 3rd-order spherical aberration |
| 14 |  | 3 | 0.00 | |
| 15 |  | 4 | 0.00 | |

*Each coefficient target value of standard Zernik coefficient

Further, when the thickness of the nerve fiber layer 114 increases or decreases depending on each subject eye, an aberration curve changes while keeping the similar shape. More specifically, the aberration curve can be defined by a mathematical function of the thickness. Therefore, it is useful to proportionally multiply each coefficient uniformly. FIG. 7 indicates the lateral aberration whose aberration coefficients are expressed by the numerical values indicated in the table 1. In this case, the position "zero" on the horizontal axis corresponds to the pupil center and the numerical value represents a distance from the pupil center. Further, the numerical value on the vertical axis indicates the lateral aberration. As illustrated in FIG. 5, a light beam shift amount at each position of the wavefront sensor 221 changes depending on the pupil position of the subject eye E. The change amount corresponds to the lateral aberration.

The following formula (1) is a mathematical function expressing the lateral aberration.

$$W(x, y) = W(\rho\sin\theta, \rho\cos\theta) = \quad (1)$$

$$W(\rho, \theta) = \sum_{n=0}^{k}\sum_{m=0}^{n} A_{nm} \cdot R_n^{n-2m}(\rho) \cdot \begin{cases} \cos|n-2m|\theta : n-2m \geq 0 \\ \sin|n-2m|\theta : n-2m < 0 \end{cases}$$

$$R_n^{n-2m}(\rho) = \sum_{s=0}^{m}(-1)^s \frac{(n-s)!\rho^{n-2s}}{s!(m-s)!(m-n-s)!} \quad (2)$$

In the formula (1), $A_{nm}$ is the standard Zernik coefficient.

Although a plurality of lenses (see FIG. 2) is used to explicitly explain the present exemplary embodiment, employing a mirror optical system is desirable when the ghost caused by lens surface reflection is taken into consideration. Further, to eliminate the cornea reflection ghost, it is desirable to provide a pinhole at an intermediate image-forming point that is in an imaging relationship with the retina of the subject eye E. In the present exemplary embodiment, the fiber light source 217 is functionally operable not only as a light source for measuring the wavefront but also as a light source for capturing an image.

The fundus imaging apparatus 200-1 according to the first exemplary embodiment acquires thickness information about the optical diffusive layer (i.e., the nerve fiber layer 114) of the fundus Er and determines the correction value to be used when the wavefront correction device 209 corrects the wavefront of the reflected light based on the acquired thickness information.

According to the above-mentioned configuration, even in a case where the optical diffusive layer of the fundus Er has a peripheral portion thicker than a central portion, it is feasible to prevent the image quality from deteriorating at the peripheral portion. Therefore, the fundus imaging apparatus 200-1 can improve the image quality of a fundus image of a subject eye.

Next, a second exemplary embodiment of the present invention will be described in detail below.

Figure 8:
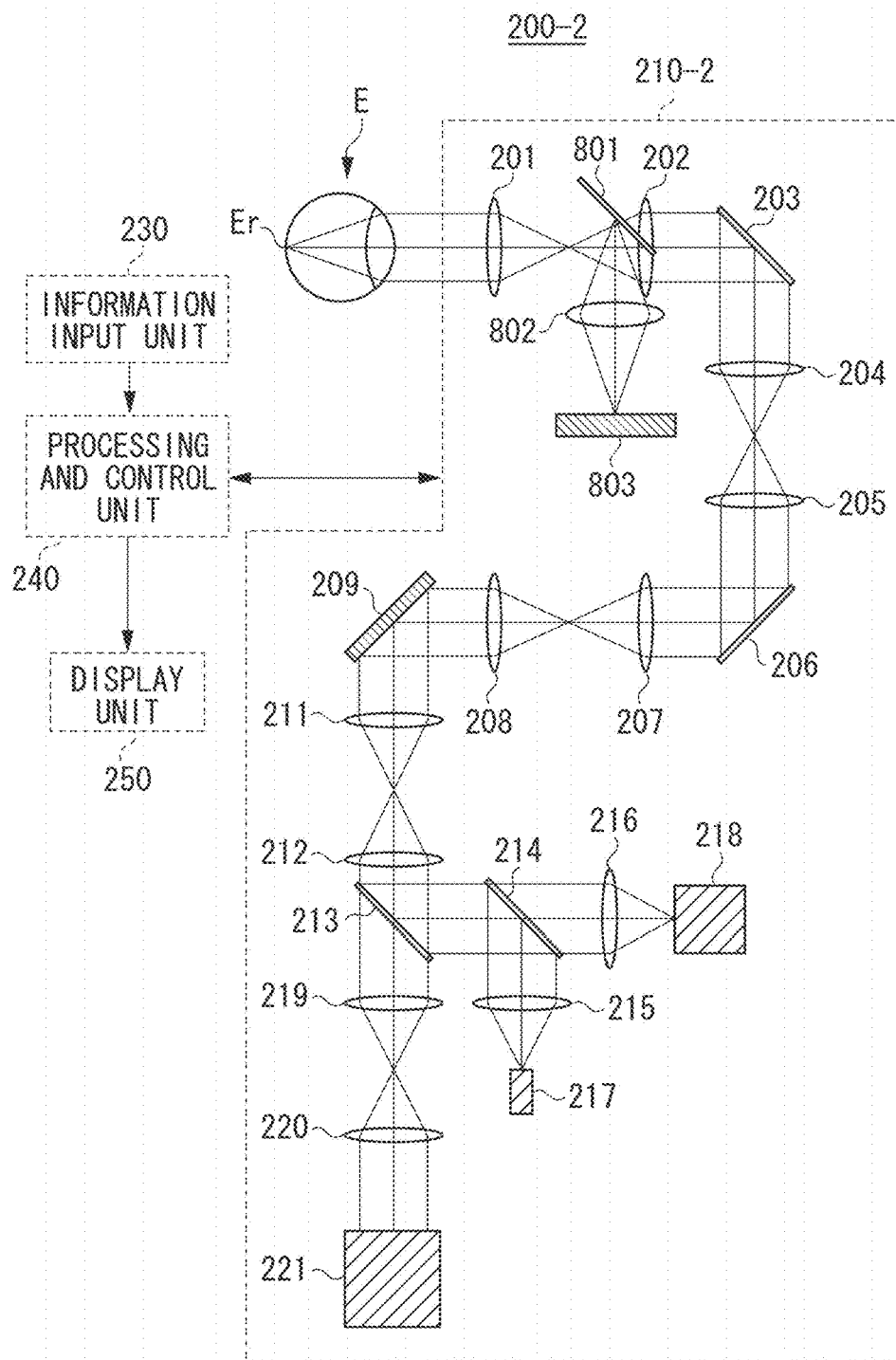
FIG. 8 illustrates an example of schematic configuration of a fundus imaging apparatus according to a second exemplary embodiment of the present invention.

FIG. 8 illustrates an example of a schematic configuration of a fundus imaging apparatus 200-2 according to the second exemplary embodiment of the present invention. In FIG. 8, constituent components similar to those illustrated in FIG. 2 are denoted by the same reference numerals and redundant description thereof will be avoided.

The fundus imaging apparatus 200-2 can capture an image of the fundus Er of the subject eye E.

As illustrated in FIG. 8, the fundus imaging apparatus 200-2 includes a fundus imaging unit 210-2, an information input unit 230, a processing and control unit 240, and a display unit 250.

The fundus imaging apparatus 200-2 according to the second exemplary embodiment illustrated in FIG. 8 is different from the fundus imaging apparatus 200-1 according to the first exemplary embodiment illustrated in FIG. 2 in that a fixation target presentation unit (see 801, 802, and 803) is provided to present fixation targets on the subject eye Er in such a way as to guide a subject line of sight and the fundus imaging apparatus estimates thickness information about the nerve fiber layer 114 by calculating an imaging position of the fundus Er, and determines a correction value to be used when the wavefront correction device 209 corrects the wavefront (i.e., wavefront aberration) of the reflected light.

More specifically, in the present exemplary embodiment, the processing and control unit 240 calculates the imaging position of the fundus Er based on a relative positional relationship between the fixation target presented by the fixation target presentation unit (see 801, 802, and 803) and an imaging portion of the APD 218 (i.e., the image-capturing unit). Then, the processing and control unit 240 acquires the thickness information about the nerve fiber layer 114 based on the imaging position of the fundus Er. In this respect, the processing and control unit 240 can serve as an acquisition unit configured to perform the above-mentioned thickness information acquisition processing.

Subsequently, the processing and control unit 240 determines the correction value (i.e., target value) to be used when the wavefront correction device 209 corrects the wavefront of the reflected light, based on the acquired thickness information about the nerve fiber layer 114. In this respect, the processing and control unit 240 can serve as the determination unit configured to determine the above-mentioned correction value.

There is a tendency that the thickness of the nerve fiber layer 114 becomes thicker on the side adjacent to the optic disk 111 and becomes thinner on the opposite side, as illustrated in FIG. 1B. The above-mentioned tendency can be confirmed with reference to many OCT real measurement data. Accordingly, it is feasible to estimate the thickness of the nerve fiber layer 114 based on the position of the fundus Er. The method according to the present exemplary embodiment is useful in that the image quality can be improved satisfactorily and it is unnecessary to provide the thickness information acquisition unit 260 separately from the fundus imaging unit 210, although the accuracy deteriorates depending on each tested eye compared to the method described in the first exemplary embodiment. Therefore, it becomes feasible to realize cost reduction and space saving.

The fixation target presentation unit illustrated in FIG. 8 includes a dichroic mirror 801, a convex lens 802, and a liquid crystal display device 803. Although the dichroic mirror 801 is disposed between the lens 201 and the lens 202 in FIG. 8, it is desirable to dispose the dichroic mirror 801 between the subject eye E and the lens 201 or between the lens 202 and the scanner 203 when dichroic angular characteristics are taken into consideration.

Figure 9:
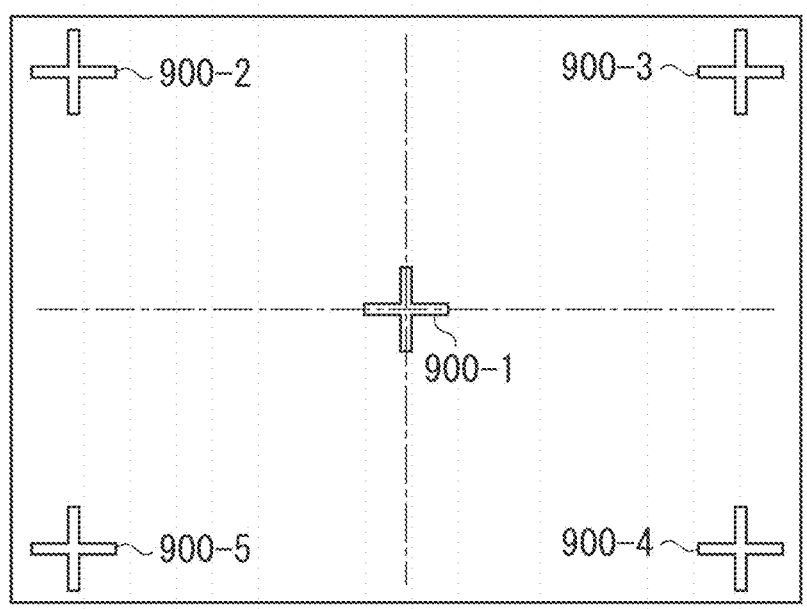
FIG. 9 illustrates an example of a fixation target image to be displayed by a liquid crystal display device illustrated in FIG. 8 according to the second exemplary embodiment of the present invention.

FIG. 9 illustrates an example of fixation target images 900-1 to 900-5 (i.e., cross-shaped targets) that can be displayed by the liquid crystal display device 803 illustrated in FIG. 8 according to the second exemplary embodiment of the present invention.

The liquid crystal display device 803 can selectively display one of the plurality of fixation target images 900-1 to 900-5 on a screen in such a way as to guide and fix the subject line of sight. FIG. 9 illustrates an example display including a central fixation target image 900-1 positioned at the center of the screen and peripheral fixation target images 900-2 to 900-5 positioned at four corners of the screen. In a case where the subject eye E is a right eye, in a state where the subject eye E gazes at the right fixation target image 900-3 or 900-4 illustrated in FIG. 9, the fundus imaging apparatus captures a partial image of the fundus Er where the thickness of the nerve fiber layer 114 is greater. Therefore, the correction values (i.e., target values) to be set in this case are numerical values offset from zero. On the other hand, when the subject eye E gazes at the left fixation target image 900-2 or 900-5 illustrated in FIG. 9, the fundus imaging apparatus captures a partial image of the fundus Er where the thickness of the nerve fiber layer 114 is very small. The correction values (i.e., target values) to be set in this case are numerical values close to zero.

The following table 2 indicates example correction values (i.e., target values) to be set when the subject eye E gazes at the fixation target image 900-3 illustrated in FIG. 9.

TABLE 2

| Term | Order | | Target coefficient | |
|---|---|---|---|---|
| | n | m | | |
| 1 | 0 | 0 | 0.00 | Constant term |
| 2* | 1 | 0 | 0.00 | Tilt X component |
| 3* | | 1 | 0.20 | Tilt Y component |
| 4 | 2 | 0 | 0.00 | Astigmatism (0°, 90°) |
| 5 | | 1 | 0.00 | Focus shift |
| 6 | | 2 | 0.00 | Astigmatism (±45°) |
| 7 | 3 | 0 | 0.00 | |
| 8 | | 1 | 0.00 | 3rd-order coma X component |
| 9* | | 2 | 0.02 | 3rd-order coma Y component |
| 10 | | 3 | 0.00 | |
| 11 | 4 | 0 | 0.00 | |
| 12 | | 1 | 0.00 | |
| 13* | | 2 | 0.03 | 3rd-order spherical aberration |
| 14 | | 3 | 0.00 | |
| 15 | | 4 | 0.00 | |

*Each coefficient target value of standard Zernik coefficient

Further, the following table 3 indicates example correction values (i.e., target values) to be set when the subject eye E gazes at the fixation target image 900-2 illustrated in FIG. 9.

TABLE 3

| Term | Order | | Target coefficient | |
|---|---|---|---|---|
| | n | m | | |
| 1 | 0 | 0 | 0.00 | Constant term |
| 2 | 1 | 0 | 0.00 | Tilt X component |
| 3 | | 1 | 0.00 | Tilt Y component |
| 4 | 2 | 0 | 0.00 | Astigmatism (0°, 90°) |
| 5 | | 1 | 0.00 | Focus shift |
| 6 | | 2 | 0.00 | Astigmatism (±45°) |
| 7 | 3 | 0 | 0.00 | |
| 8 | | 1 | 0.00 | 3rd-order coma X component |
| 9 | | 2 | 0.00 | 3rd-order coma Y component |
| 10 | | 3 | 0.00 | |
| 11 | 4 | 0 | 0.00 | |
| 12 | | 1 | 0.00 | |
| 13 | | 2 | 0.00 | 3rd-order spherical aberration |
| 14 | | 3 | 0.00 | |
| 15 | | 4 | 0.00 | |

Further, even in the present exemplary embodiment, it is desired to employ the mirror optical system when the ghost is taken into consideration as mentioned in the first exemplary embodiment. Further, similar to the first exemplary embodiment, it is desirable to provide a pinhole at an intermediate image-forming point that is in an imaging relationship with the retina of the subject eye E.

According to the second exemplary embodiment, similar to the first exemplary embodiment, even in a case where the optical diffusive layer of the fundus Er has a thicker peripheral portion, it is feasible to prevent the image quality from deteriorating at the peripheral portion. Therefore, the fundus imaging apparatus 200-2 can improve the image quality of a fundus image of a subject eye.

Next, a third exemplary embodiment of the present invention will be described in detail below.

Figure 10:
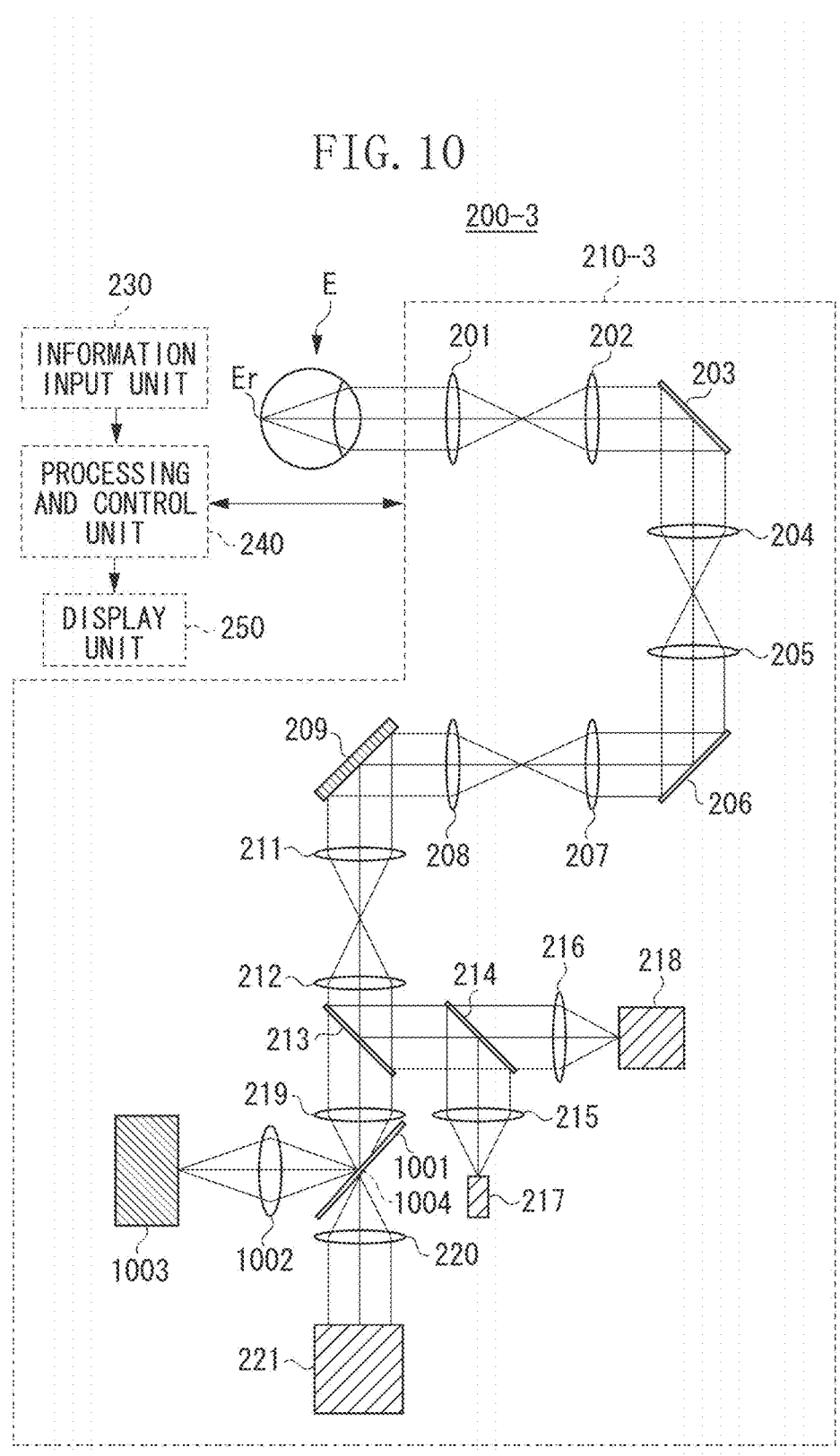
FIG. 10 illustrates an example of a schematic configuration of a fundus imaging apparatus according to a third exemplary embodiment of the present invention.

FIG. 10 illustrates an example of a schematic configuration of a fundus imaging apparatus 200-3 according to the third exemplary embodiment of the present invention. In FIG. 10, constituent components similar to those illustrated in FIGS. 2 and 8 are denoted by the same reference numerals and redundant description thereof will be avoided.

The fundus imaging apparatus 200-3 can capture an image of the fundus Er of the subject eye E.

As illustrated in FIG. 10, the fundus imaging apparatus 200-3 includes a fundus imaging unit 210-3, an information input unit 230, a processing and control unit 240, and a display unit 250.

The fundus imaging apparatus 200-3 according to the third exemplary embodiment illustrated in FIG. 10 is different from the fundus imaging apparatus 200-1 according to the first exemplary embodiment illustrated in FIG. 2 and the fundus imaging apparatus 200-2 according to the second exemplary embodiment illustrated in FIG. 8 in that an observation unit (see 1001, 1002, and 1003) is provided between the wavefront sensor 221 and the subject eye E to observe a reflected light intensity distribution at an intermediate image-forming point 1004 and a position conjugate with the fundus Er (retina).

Further, in the present exemplary embodiment, the processing and control unit 240 can acquire information about the thickness of the optical diffusive layer (i.e., the nerve fiber layer 114) of the fundus Er based on the reflected light intensity distribution obtained by the above-mentioned observation unit. In this respect, the processing and control unit 240 can serve as the acquisition unit configured to perform the above-mentioned thickness information acquisition processing.

Subsequently, the processing and control unit 240 can determine a correction value (target value) to be used when the wavefront correction device 209 corrects the wavefront of the reflected light, based on the acquired thickness information about the nerve fiber layer 114. In this respect, the processing and control unit 240 can serve as the determination unit configured to determine the above-mentioned correction value.

The observation unit illustrated in FIG. 10 includes a beam splitter 1001, a convex lens 1002, and a light detector 1003.

The beam splitter 1001 according to the present exemplary embodiment has a transmittance of 70% and a reflectance of 30%, so that a greater amount of light can be input to the wavefront sensor 221.

The convex lens 1002 can form an image of the light of the intermediate image-forming point 1004 on the light detector 1003.

The light detector 1003 can detect the reflected light intensity distribution. The reflected light intensity distribution detected by the light detector 1003 will be described in detail below with reference to FIGS. 11A and 11B.

Figure 11A:
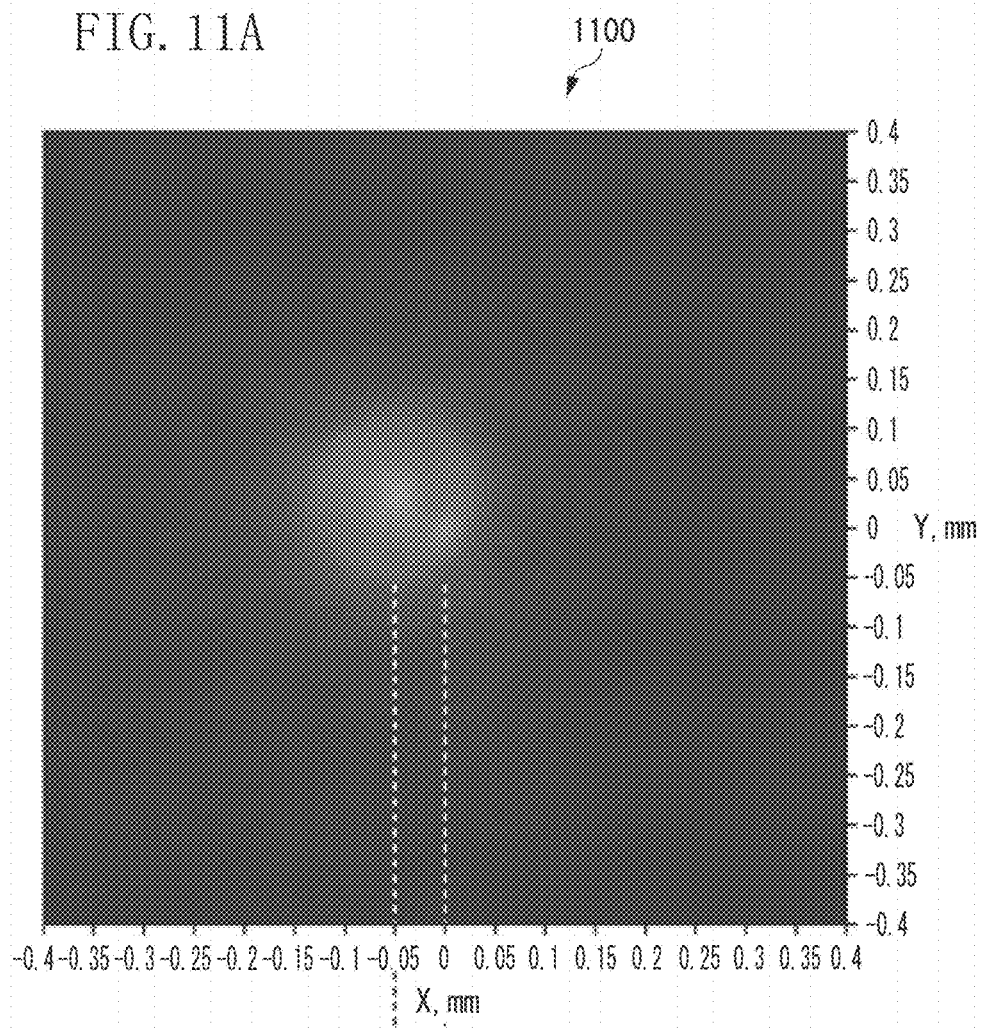
FIGS. 11A and 11B illustrate a reflected light intensity distribution at an intermediate image-forming point illustrated in FIG. 10 according to the third exemplary embodiment of the present invention.
Figure 11B:
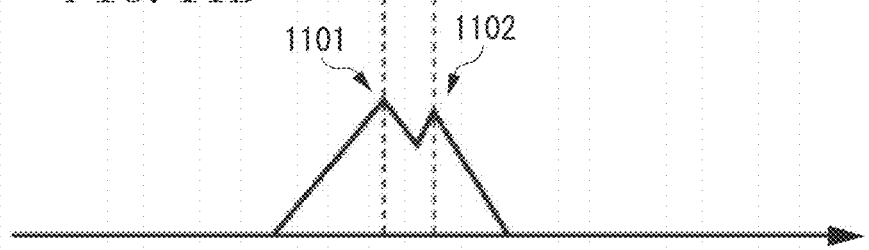

FIGS. 11A and 11B illustrate an example of the reflected light intensity distribution at the intermediate image-forming point 1004 illustrated in FIG. 10 according to the third exemplary embodiment of the present invention. FIG. 11A illustrates a light intensity distribution image 1100 of the reflected light, and FIG. 11B illustrates the light intensity distribution.

The nerve fiber layer 114 and the photoreceptor cell layer 113 of the fundus Er possess optical diffusibility. Therefore, the light intensity distribution at the intermediate image-forming point 1004 is a gentle distribution as illustrated in FIG. 11B. More specifically, two bright spots 1101 and 1102 corresponding to the light beams reflected on the nerve fiber layer 114 and the photoreceptor cell layer 113 can be observed from the light intensity distribution illustrated in FIG. 11B.

As described in the first exemplary embodiment, the light enters the subject eye E from a point offset from the pupil center and illuminates the fundus Er. Therefore, dummy light emission points of the nerve fiber layer 114 and the photoreceptor cell layer 113 are formed at mutually shifted positions. In this case, the wavefront may be erroneously measured as mentioned in the first exemplary embodiment.

Figure 12:
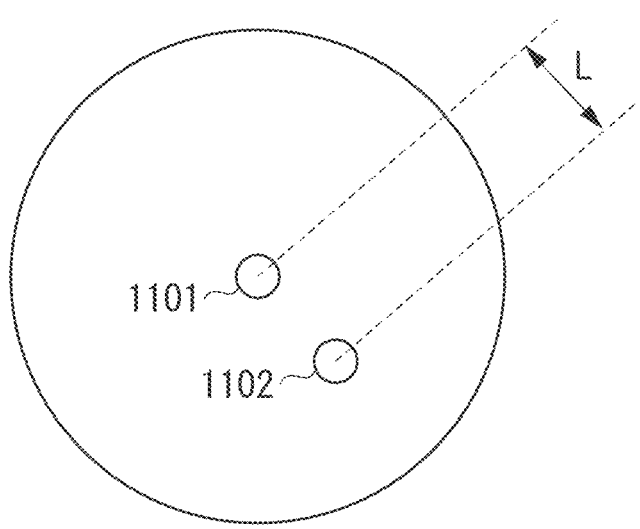
FIG. 12 illustrates a distance between two bright spots illustrated in FIG. 11 according to the third exemplary embodiment of the present invention.

FIG. 12 illustrates a distance L between two bright spots 1101 and 1102 illustrated in FIG. 11B according to the third exemplary embodiment of the present invention.

The processing and control unit 240 calculates the distance L between two bright spots 1101 and 1102 illustrated in FIG. 12 through image analysis processing applied to the light intensity distribution image 1100 illustrated in FIG. 11A. The distance L is longer when the nerve fiber layer 114 is thick and is shorter when the nerve fiber layer 114 is thin. Accordingly, the processing and control unit 240 can acquire the thickness information about the nerve fiber layer 114 by calculating the distance L. Then, if the acquisition of the thickness information about the nerve fiber layer 114 completes, an aberration amount erroneously detected as the wavefront aberration can be known as described in the first exemplary embodiment. Therefore, the fundus imaging apparatus can accurately perform wavefront aberration correction. By causing the observation unit to observe the reflected light intensity distribution at the intermediate image-forming point 1004, the processing and control unit 240 can acquire the thickness information about the nerve fiber layer 114. Subsequently, the processing and control unit 240 determines the correction value (i.e., target value) to be used when the wavefront correction device 209 corrects the wavefront of the reflected light. Thus, the fundus imaging apparatus can adequately perform eyeball aberration correction.

Next, an example procedure of image capturing processing that can be performed by the fundus imaging apparatus 200-3 will be described in detail below.

First, in a state where the subject eye E is fixedly placed on the fundus imaging apparatus 200-3, the wavefront sensor 221 measures the wavefront (i.e., wavefront aberration) of reflected light guided via the above-mentioned optical unit when the light is emitted from the fiber light source 217 and reflected on the fundus Er. Further, at the same time, the processing and control unit 240 acquires thickness information about the nerve fiber layer 114 with reference to the reflected light intensity distribution at the intermediate image-forming point 1004 obtained by the light detector 1003, and determines the correction value (i.e., target value) to be used when the wavefront correction device 209 corrects the wavefront (i.e., wavefront aberration) of the reflected light based on the acquired thickness information about.

Subsequently, the processing and control unit 240 corrects the wavefront of the reflected light measured by the wavefront sensor 221, by driving the wavefront correction device 209 based on the determined correction value. Then, the processing and control unit 240 stops the operation of the wavefront correction device 209 at the time when the wavefront correction has been performed based on the correction value determined by the wavefront correction device 209, and controls the APD 218 to perform an image capturing operation.

Further, even in the present exemplary embodiment, employing the mirror optical system is desirable when the ghost is taken into consideration as mentioned in the first exemplary embodiment. Further, similar to the first exemplary embodiment, it is desirable to provide a pinhole at an intermediate image-forming point that is in an imaging relationship with the retina of the subject eye E.

According to the third exemplary embodiment, similar to the first exemplary embodiment, even in a case where the diffusibility possession layer of the fundus Er has a thick peripheral portion, the fundus imaging apparatus can prevent the image quality from deteriorating at a peripheral portion. In other words, the fundus imaging apparatus can improve the image quality of a fundus image of a subject eye.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-028252, filed Feb. 17, 2016, which is hereby incorporated by reference herein in its entirety.

What is claimed is:
1. A fundus imaging apparatus configured to capture a fundus image of a subject eye, the apparatus comprising:

an optical unit configured to guide light from a light source to a fundus;

a wavefront measurement unit configured to measure the wavefront of reflected light guided via the optical unit after the light is reflected on the fundus;

a wavefront correction unit provided on an optical path extending between the light source and the subject eye and configured to correct the wavefront;

an image-capturing unit configured to receive the reflected light and capture an image of the fundus;

an acquisition unit configured to acquire thickness information about an optical diffusive layer of the fundus; and a determination unit configured to determine a correction value to be used when the wavefront correction unit corrects the wavefront based on the thickness information.

2. The fundus imaging apparatus according to claim 1, wherein the acquisition unit acquires thickness information about a specific optical diffusive layer of the fundus, which is positioned closest to incoming light when the light enters the fundus.

3. The fundus imaging apparatus according to claim 1, wherein the wavefront measurement unit measures the wavefront of light reflected on at least two optical diffusive layers of the fundus.

4. The fundus imaging apparatus according to claim 1, wherein the wavefront correction unit corrects the wavefront of the reflected light that enters the image-capturing unit.

5. The fundus imaging apparatus according to claim 1, further comprising a fixation target presentation unit configured to present a fixation target on the subject eye in such a way as to guide a subject line of sight, wherein the acquisition unit acquires the thickness information with reference to an imaging position of the fundus, which can be calculated based on a relative positional relationship between the fixation target and an imaging portion of the image-capturing unit.

6. The fundus imaging apparatus according to claim 1, wherein the acquisition unit acquires thickness information about a nerve fiber layer, which is one of optical diffusive layers of the fundus.

7. The fundus imaging apparatus according to claim 1, further comprising an observation unit configured to observe a reflected light intensity distribution at a position conjugate with the fundus, which is positioned between the wavefront measurement unit and the subject eye, wherein the acquisition unit acquires the thickness information about the optical diffusive layer of the fundus based on the reflected light intensity distribution.

8. The fundus imaging apparatus according to claim 1, wherein the wavefront correction unit corrects the wavefront based on the correction value determined by the determination unit.

9. A method for controlling a fundus imaging apparatus that includes an optical unit configured to guide light from a light source to a fundus of a subject eye, a wavefront measurement unit configured to measure the wavefront of reflected light guided via the optical unit after the light is reflected on the fundus, a wavefront correction unit provided on an optical path extending between the light source and the subject eye and configured to correct the wavefront, and an image-capturing unit configured to receive the reflected light and capture an image of the fundus, the method comprising:

acquiring thickness information about an optical diffusive layer of the fundus, and determining a correction value to be used when the wavefront correction unit corrects the wavefront based on the thickness information.

10. A computer readable storage medium for storing a program that causes a computer to perform a control method for a fundus imaging apparatus that includes an optical unit configured to guide light from a light source to a fundus of a subject eye, a wavefront measurement unit configured to measure the wavefront of reflected light guided via the optical unit after the light is reflected on the fundus, a wavefront correction unit provided on an optical path extending between the light source and the subject eye and configured to correct the wavefront, and an image-capturing unit configured to receive the reflected light and capture an image of the fundus, the control method comprising:

acquiring thickness information about an optical diffusive layer of the fundus; and determining a correction value to be used when the wavefront correction unit corrects the wavefront based on the thickness information.

* * * * *